(12) United States Patent
Passi et al.

(10) Patent No.: US 6,303,139 B1
(45) Date of Patent: Oct. 16, 2001

(54) DIETARY PRODUCT EFFECTIVE TO COMBAT OXIDATIVE STRESS AND CELL DECAY

(75) Inventors: Siro Passi, Rome; Decimo Guarnieri, Pomezia; Santo Carbone, Latina, all of (IT)

(73) Assignee: IDI Farmaceutici S.p.A., Pomezia (IT)

(*) Notice: Subject to any disclaimer, the term of this patent is extended or adjusted under 35 U.S.C. 154(b) by 0 days.

(21) Appl. No.: 09/355,558

(22) PCT Filed: Feb. 2, 1998

(86) PCT No.: PCT/IT98/00015

§ 371 Date: Jul. 30, 1999

§ 102(e) Date: Jul. 30, 1999

(87) PCT Pub. No.: WO98/33495

PCT Pub. Date: Aug. 6, 1998

(30) Foreign Application Priority Data

Jan. 31, 1997 (IT) .............................. RM97A0045

(51) Int. Cl.[7] .............. A61K 9/28; A61K 9/68; A61K 47/00

(52) U.S. Cl. ............... 424/441; 424/439; 424/450; 424/464

(58) Field of Search ................... 424/439, 441, 424/450, 464

(56) References Cited

FOREIGN PATENT DOCUMENTS

0519876 * 12/1992 (EP).
WO 96/17626 * 12/1992 (WO).

* cited by examiner

*Primary Examiner*—Thurman K. Page
*Assistant Examiner*—S. Howard
(74) *Attorney, Agent, or Firm*—Browdy and Neimark

(57) ABSTRACT

The present invention relates to a dietary product comprising ubiquinone, stabilized vitamin E, phospholipids, selenuim in an organic form and L-methionin, which is effective to combat cell oxidative stress even to the extreme consequences thereof, for example cell decay, acquired and/or congenital immunodeficiency or other alterations in the immune system. The dietary product object of the present invention is also effective as a coadjutant in the treatment of apoptosis, in mutagenesis and/or carcinogenesis, in infectious diseases of viral or bacterial origin or those deriving from other external pathogens, in myelinic and skin diseases, in cardiovascular diseases and in allergies.

21 Claims, 15 Drawing Sheets

DIETARY PRODUCT EFFECTIVE TO COMBAT OXIDATIVE STRESS AND CELL DECAY

CROSS REFERENCE TO RELATED APPLICATION

The present application is the national stage under 35 U.S.C. 371 of PCT/IT98/00015, filed Feb. 2, 1998.

The cell antioxidant pool is essentially made up of enzymatic antioxidants (Cu—Zn, superoxide dismutase—SOD, glutathione peroxidase-GSH-Px, catalase-CAT), of non-enzymatic lipophilic (RRR-α-tocopherol-vitamin E and ubiquinol-$CoQ_{10}H_2$—) and hydrophilic (glutathione-GSH, urates, albumin) antioxidants and of protic transition metal ion sequestrating agents (ferrite, transferring, ceruloplasmin) see bibliographic references 1–7).

Each molecule has a specific biological function: for example the vitamin E and the ubiquinol are concentrated in the cell and sub-cell membranes with the main role of inhibiting lipo-peroxidation induced by oxygen reactive species (ROS) and other radicals on the unsaturated structures of the membranes, in particular the polyunsaturated fatty acids (PUFA); SOD, GSG-Px and CAT are responsible for removal of $O_2$ and $H_2O_2$, respectively.

Human cells have an antioxidant pool sufficient to counteract the normal physiological production of oxygen reactive species (ROS) and other free radicals; however the naturally present antioxidant pool is not capable of counteracting an increase in generation of ROS; in these cases, so-called "oxidative stress" occurs (see bibliographic reference 2).

From the above it can be seen that the insurgence of "oxidative stress" can be caused by two phenomena: the first is the lack of antioxidant molecules, and the second is the uncontrolled increase of oxygen reactive species (ROS) and free radicals, which are able to cause irreversible oxidation not only of the polyunsaturated fatty acids (PUFA), but also of proteins, nucleic acids and sugars. Oxidative stress is present to a varied extent in a number of serious diseases in man: while this does not mean that oxidative stress is the cause of these diseases, it does testify, as confirmed by a number of studies, that oxidative stress can have a negative influence on the progress of said diseases, causing further damage to the cells of an organism that is already sick (see bibliography and references 1 and 2).

It has now surprisingly been found that a dietary product comprising ubiquinone ($CoQ_{10}$), stabilized vitamin E, phospholipids, selenium of organic origin and L-methionine, by acting both on the call wall reconstitution mechanisms, and consequently on that of the phospholipids forming it, and on the reintegration of glutathione and glutathione peroxidase, helps to combat cellular oxidative stress in an effective manner.

Oxidative stress appears significantly involved in certain diseases with a serious social impact, such as AIDS, seborrheic dermatitis, atopic dermatitis, leprosy, multiple sclerosis, in which genetic factors, malnutrition and/or under-nourishment, an incongruous lifestyle, the use of drugs and toxic substances, have an important etiologic role. It has been found that in the blood of patients suffering from these diseases, the significant deficiency of ubiquinole-ubiquinone, vitamin E, glutathione and glutathione peroxidase (GSH and GSH-Px), which is more or less marked according to contingent conditions, is associated with a deficiency of polyunsaturated fatty acids (PUFA) in the phospholipids (see references 8–12). According to the state of the art, administration of the molecules identified above to patients suffering from seborrheic and atopic dermatitis is simply and generally described, although said administration takes place in a separate and non-homogeneous manner, and this type of administration has actually shown extremely promising results (see references 11–12).

SUMMARY OF THE INVENTION

An object of the present invention is therefore a composition comprising:

| | |
|---|---|
| Ubiquinone | 5–8% |
| Stabilized vitamin E | 12–15% |
| Polyunsaturated phospholipids | 45–52% |
| Organic selenium | 2–5% (corresponding to 0.1–3% ionic selenium) |
| L-methionine | 23–32% | along with the usual tolerated vehicles.

A further object of the present invention is a composition for a dietary product comprising:

| | |
|---|---|
| Ubiquinone | 5–8% |
| Stabilized vitamin E | 12–15% |
| Polyunsaturated phospholipids | 45–52% |
| Organic selenium | 2–5% (corresponding to 0.1–3% ionic selenium) |
| L-methionine | 23–32% | along with the usual pharmaceutically tolerated vehicles.

The percentages indicated are expressed as a percentage by weight with reference only to the total weight of the active ingredients in the composition of the dietary product.

A further object of the present invention is the use of the composition for preparation of a dietary product that is effective in combating oxidative stress and cell decay.

A further object of the present invention is the use of the composition indicated above to produce a dietary product effective as a coadjutant in the treatment of mechanisms of mutagenesis and carcinogenesis, of immune-deficiency mechanisms, or other alterations of the immune system, of diseases of myelinic origin or other pathologies deriving from a progressive alteration in the neurotransmission mechanisms, of skin diseases and of cardio-vascular diseases.

A further object of the present invention is the use of the composition mentioned above to prepare a dietary product in the treatment of infectious diseases of viral or bacterial origin, and those deriving from other external pathogens, of tuberculosis, of leprosy, of herpes simplex labialis or genitalia, of AIDS, of multiple sclerosis, or atopic dermatitis, of vitiligo, in vaccination against allergies or other alterations of the immune system, of diseases of myelinic origin or other pathologies deriving from a progressive alteration in the neurotransmission mechanisms.

The present description comprises fifteen figures which show, in graph form, the influence of administration of a composition according to the present invention to the patients who will be more clearly specified in example 3 in case of FIGS. 1 to 9 and in example 4 in case of FIGS. 10 to 15:

Figure 1:
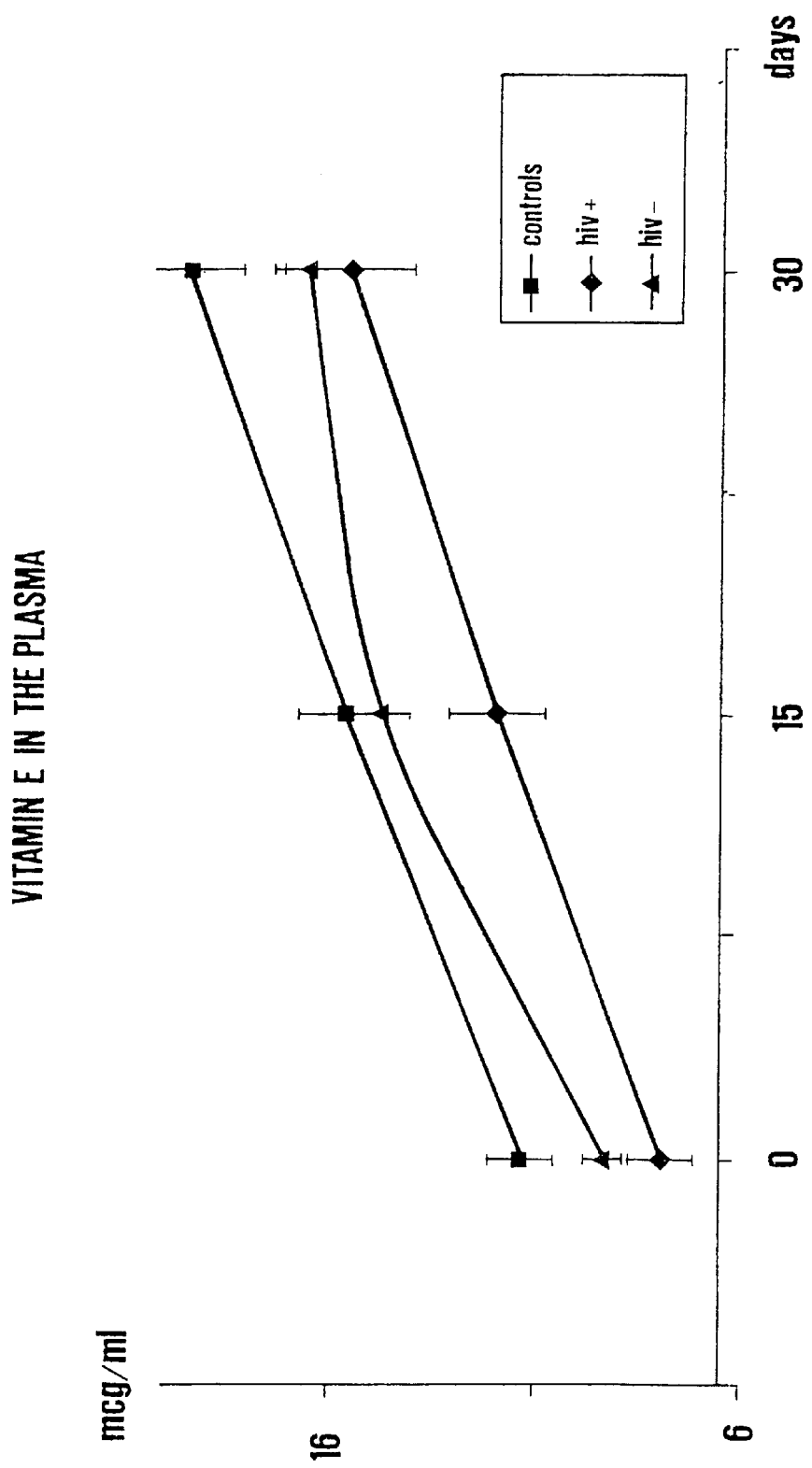
FIG. 1 shows the vitamin E concentration in the blood plasma versus time.
Figure 2:
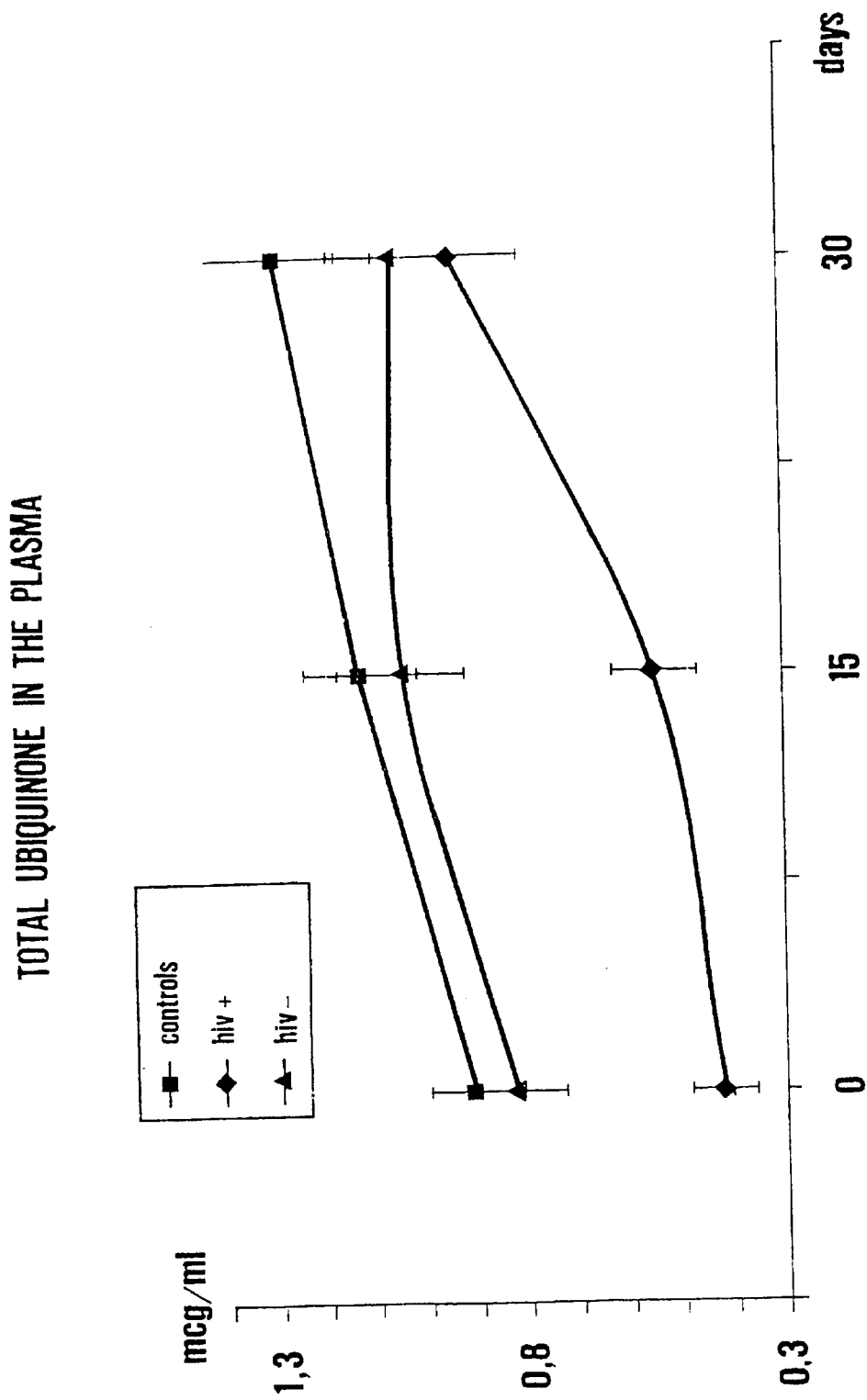
FIG. 2 shows the blood plasma concentration of oxidized and reduced ubiquinone (total ubiquinone) versus time.

In the following examples concerning the production, composition and formulation of compositions for dietary products according to the present invention as well as the evaluation of the effect of its administration are reported.

EXAMPLE 1

The present example relates to the production of a pill with the following qualitative and quantitative composition:

| Ubiquinone | mg 12.50 (6.74% by weight) |
| RRR-α-tocopheryl acetate 50% | mg 26.65 (14.37% by weight) |
| Soy lecithin | mg 90.00 (48.54% by weight) |
| Selenium aspartate | mg 6.25 (3.37% by weight) |
| L-methionine | mg 50.00 (26.97% by weight) |
| Other excipients to make | g 1.50 |

The percentage expressed refer to the total weight of the active components of the composition, without taking into account the excipients. Particularly preferred excipients are those that can be used to formulate a compound that can be chewed; among said excipients it is possible to mention mannitol, cellulose, flavouring, magnesium stearate, silica. The vitamin E acetate is of the type obtained by direct compression, and it is therefore combined with 50% of inert substances suitable to help compression.

The amount of selenium aspartate indicated corresponds to 12.5 μg of selenium in ionic form. Excipients are added to the above mixture of components, which are then subjected to a further mixing stage, and following this to compression in the laboratory. Pills of 1.5 g each are obtained, with a thickness of 6 mm.

EXAMPLE 2

Preparation of an industrial batch of pills having the same qualitative and quantitative composition described in example 1.

| Ubiquinone | kg 1.250 |
| RRR-α-tocopheryl acetate 50% | kg 2.665 |
| Soy lecithin | kg 9.000 |
| Selenium aspartate | kg 0.625 |
| L-methionine | kg 5.000 |
| Other excipients to make | kg 150 |

To the mixture of components listed above are added the excipients (mannitol, cellulose, flavouring, magnesium stearate, silica). A further mixing stage is then performed, after which the pills are formed using an industrial press of a per se know type. Pill weighing 1.5 g each and with a thickness of 6 mm are obtained.

The polyunsaturated fatty acids and the vitamin E employed in the compositions according to the present invention have been analysed by means of capillary gas chromatography-mass spectrometry (see reference 8). The ubiquinole/ubiquinone and GSH/GS-SG redox pairs by HPLC (see references 13–14); the superoxide dismutase, glutathione peroxidase and catalase activities (respectively SOD, GSH-Px and CAT) by spectrophotometry (see references 15–17) using the procedures indicated in each of the relative references. The vitamin E used in the composition of the dietary product according to the present invention was analysed both in the composition and in the blood plasma after administration, by means of HPLC on chiral phase (see bibliographic reference No. 18).

EXAMPLE 3

This example gives an evaluation of the effects of administration of four pills per day, with the following qualitative and quantitative composition, to a certain number of volunteers who will be further described in the following.

The composition was as follows:

| Ubiquinone | mg 12.50 |
| RRR-α-tocopheryl acetate 50% | mg 26.65 |
| Soy lecithin | mg 90.00 |
| Selenium aspartate | mg 6.25 |
| L-methionine | mg 50.00 |
| Other excipients to make | g 1.50 |

The pills were administered daily during meals, for one month to 60 volunteers, half male and half female, aged between 25 and 42 years. The volunteers represented the following: 20 healthy individuals (controls), 20 seropositive HIV patients (HIV+) suffering from seborrheic dermatitis (DS), 20 seronegative HIV patients (HIV−) also suffering from seborrheic dermatitis.

A diet rich in polyunsaturated fatty acids was recommended for the patients suffering from seborrheic dermatitis. At the start of treatment, after 15 days and 30 days after the end of treatment the following parameters were measured for each individual:

a) The blood levels of phospholipids-polyunsaturated fatty acids, vitamin E, oxidized and reduced ubiquinone (total ubiquinone);

b) The levels of vitamin E in the lymphocytes;

c) Superoxide dismutase (SOD), catalase (CAT) and glutathione peroxidase (GSH-Px) activity in the erythrocytes;

d) The levels of reduced and oxidized glutathione (GSH and GS-SG) in the erythrocytes. The results are shown in the following tables 1 and 2, and exemplified in FIGS. 1, 2, 3, 4, 5, 6, 7, 8, and 9.

Figure 3:
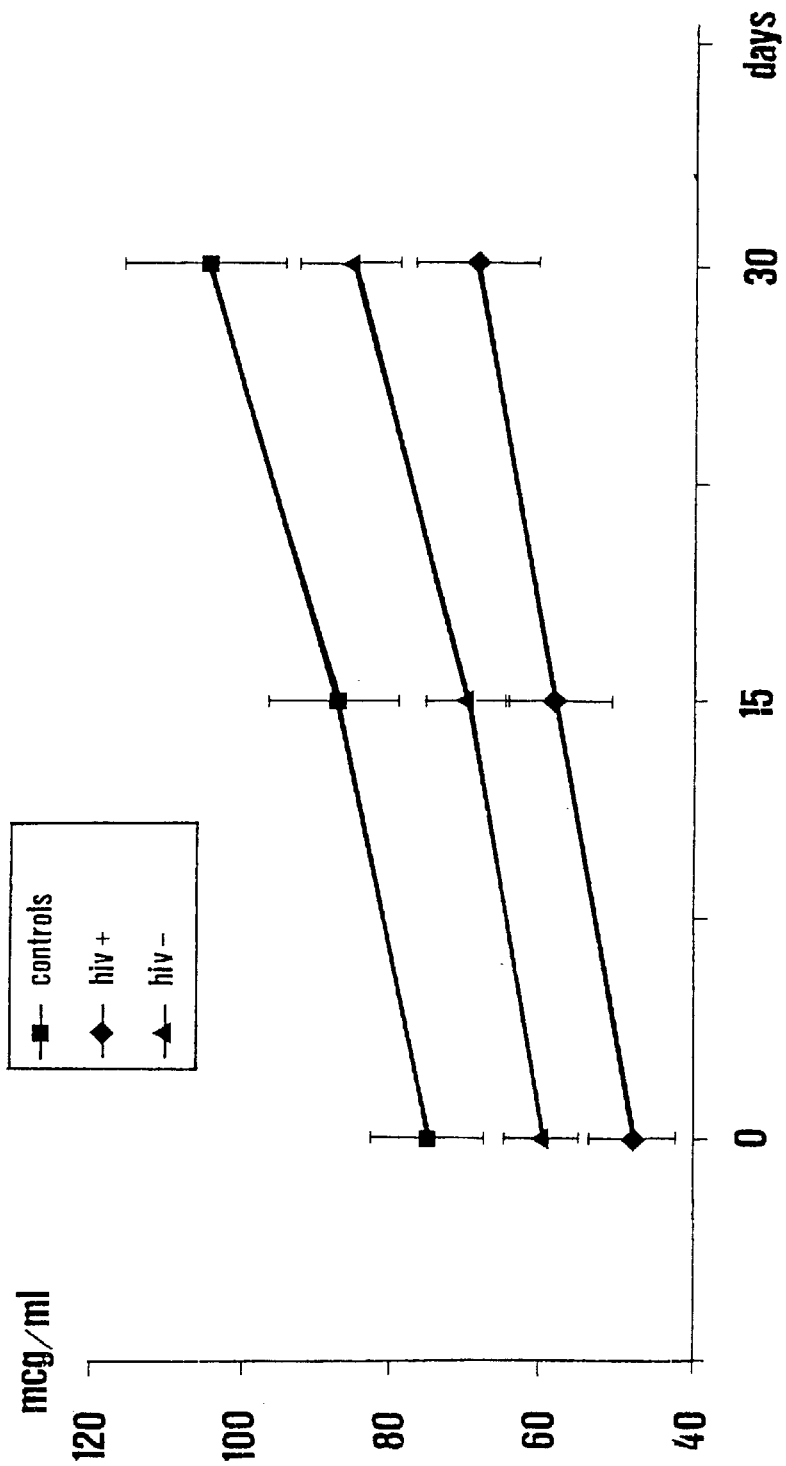
FIG. 3 shows the concentration of vitamin E (expressed as micrograms of vitamin E in the lymphocytes per ml of blood) in the lymphocytes versus time.
Figure 4:
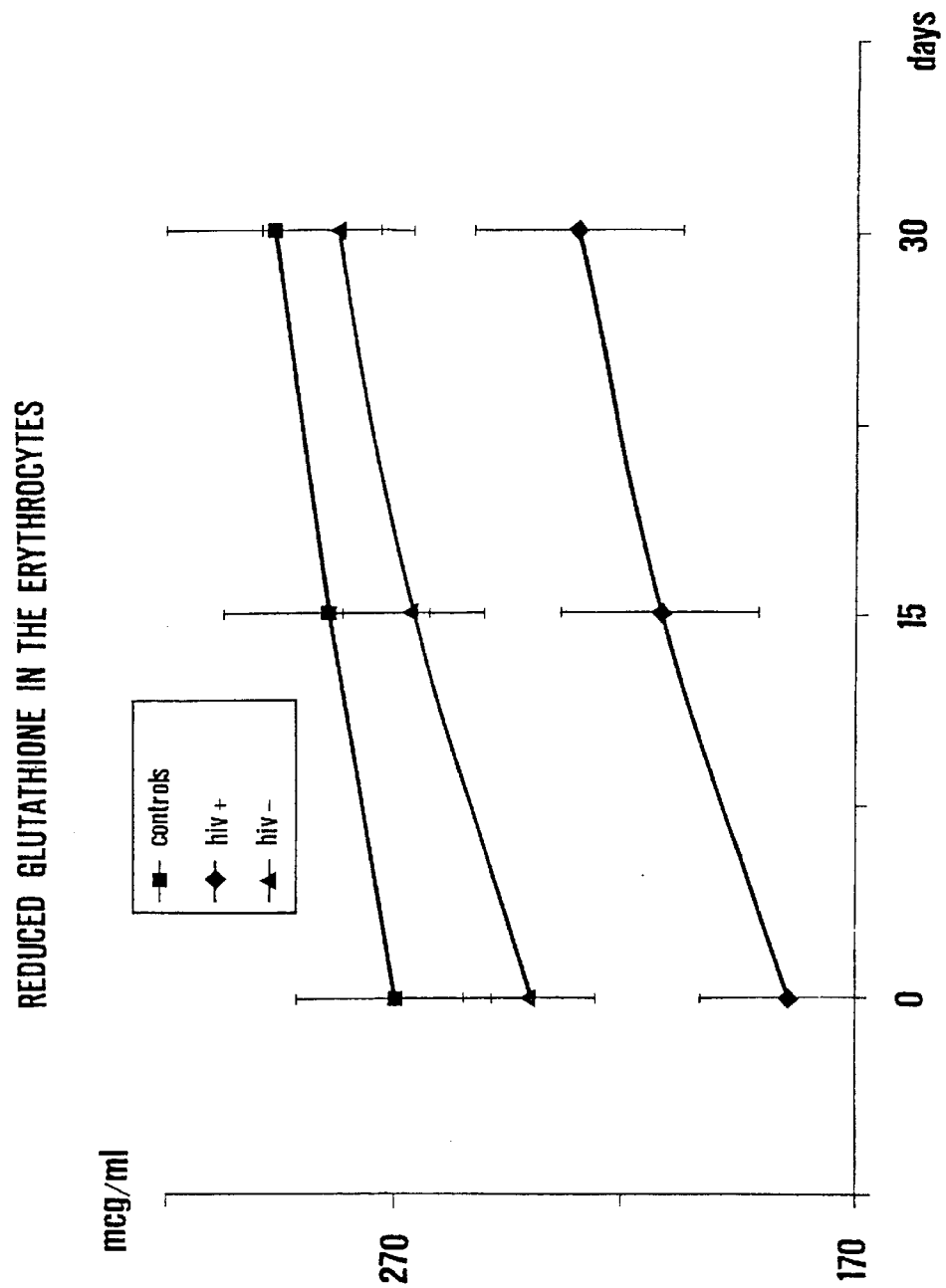
FIG. 4 shows the reduced glutathione concentration in the erythrocytes versus time.
Figure 5:
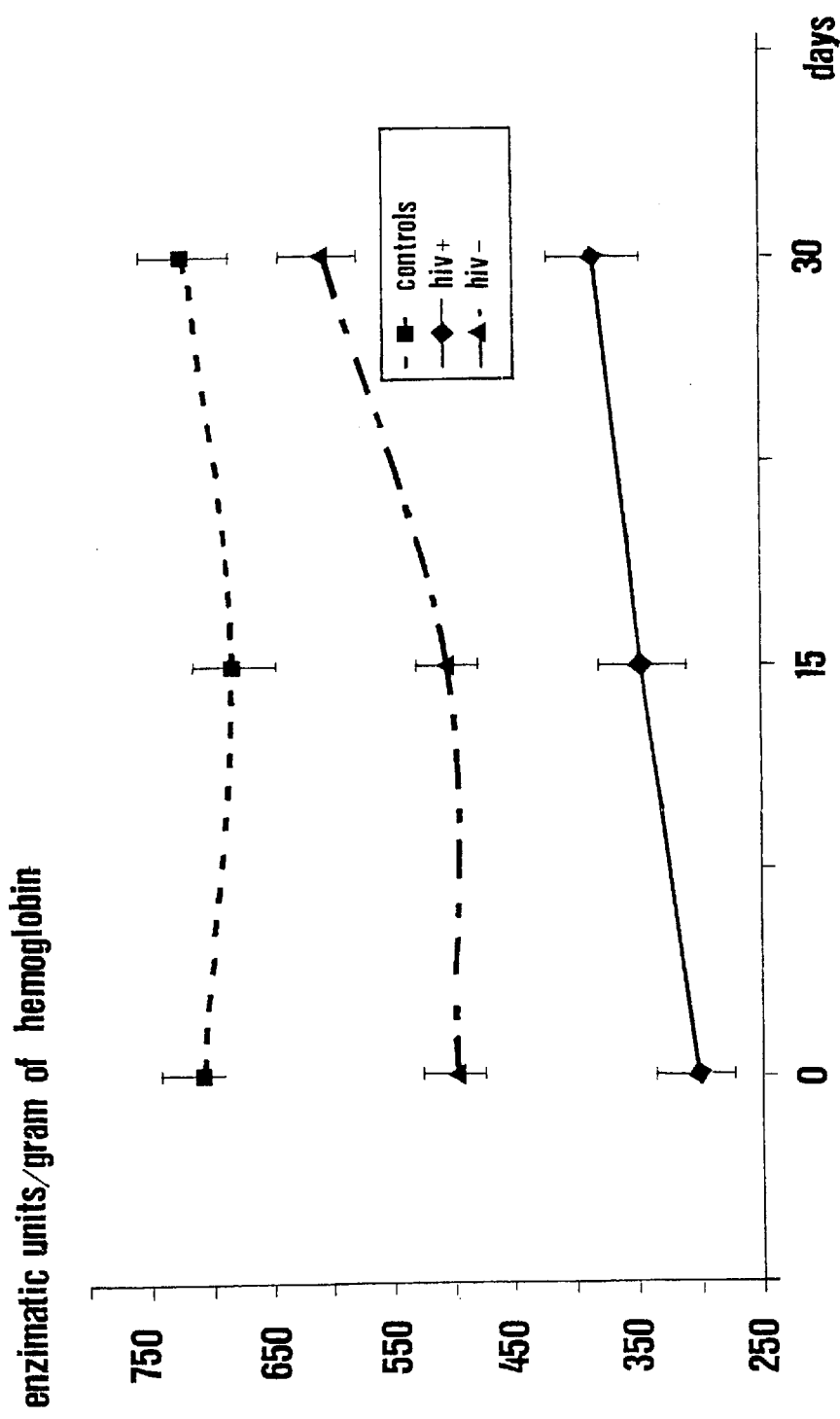
FIG. 5 shows the glutathione peroxidase concentration in the erythrocytes versus time.
Figure 6:
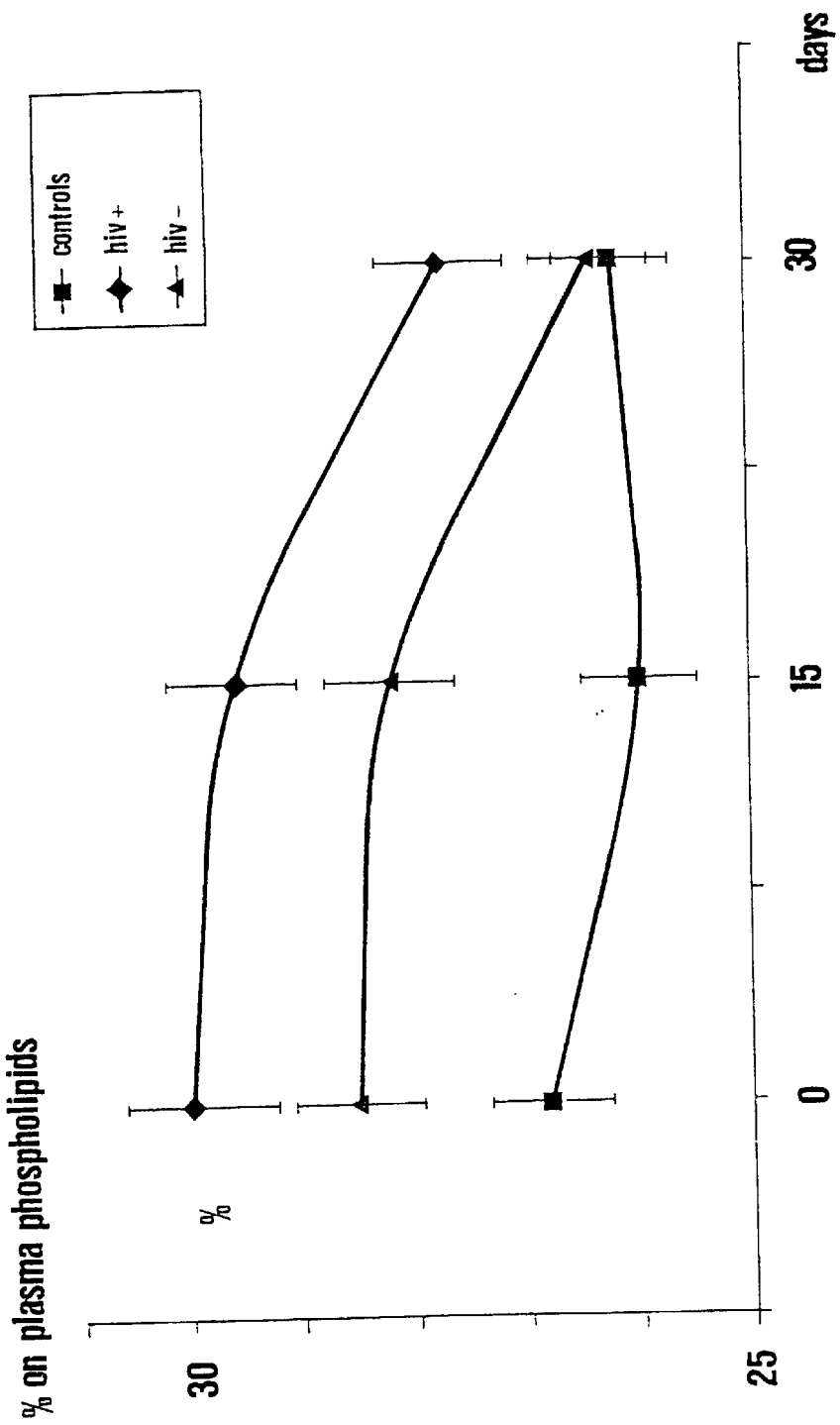
FIG. 6 shows the trend of the palmitic acid concentration in the plasma versus time.
Figure 7:
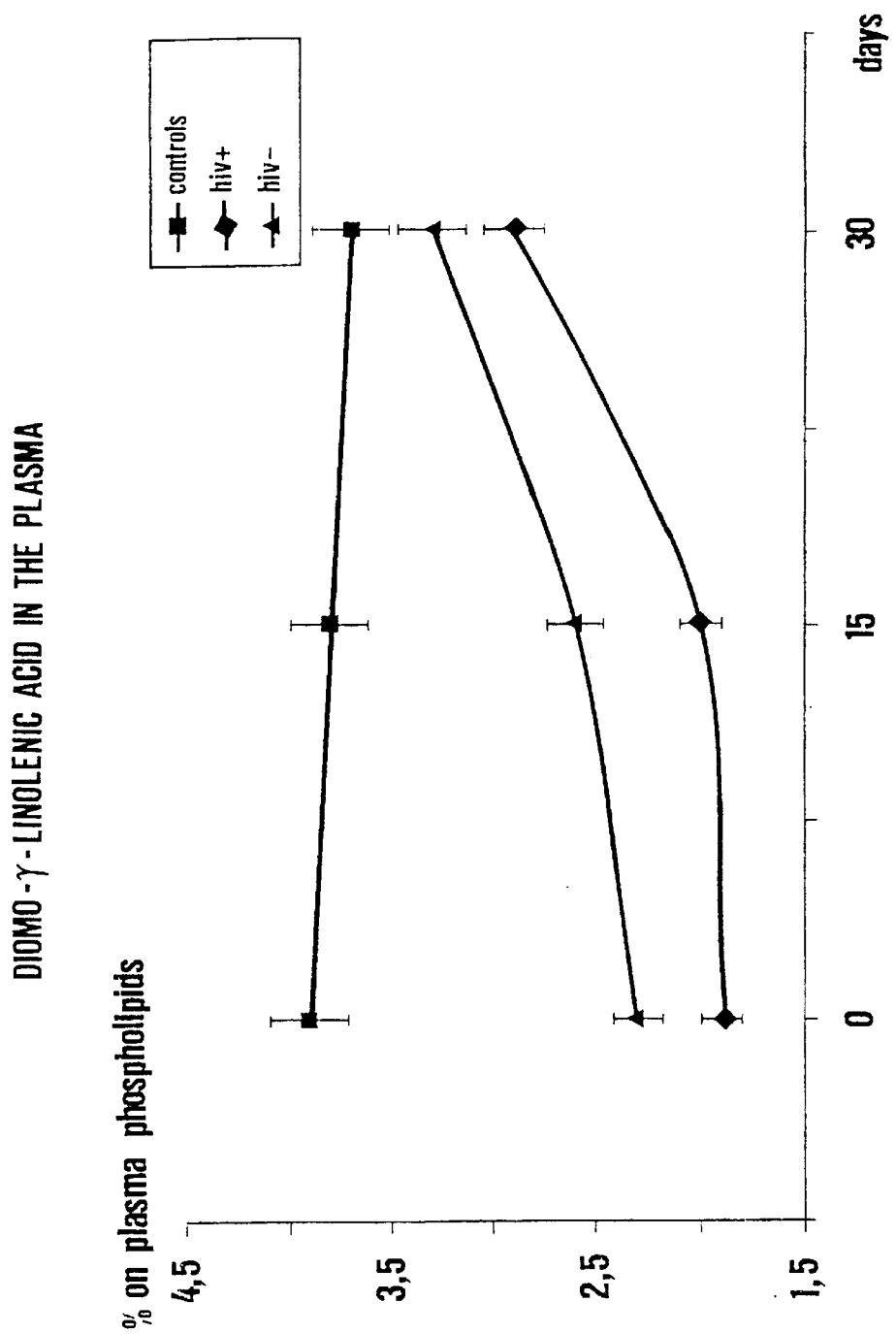
FIG. 7 shows the trend of the diomo-γ-linolenic acid concentration in the plasma versus time.
Figure 8:
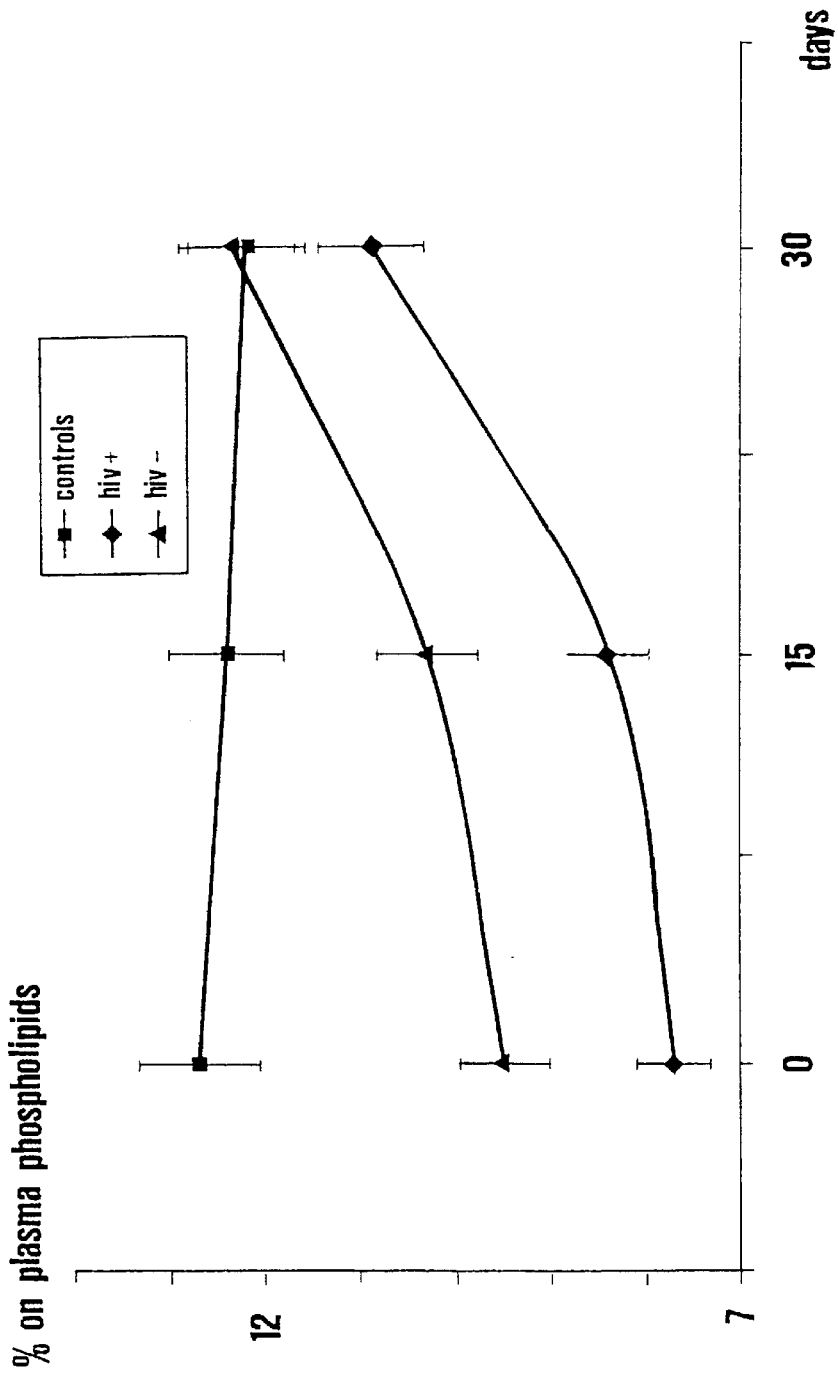
FIG. 8 shows the trend of the arachidonic acid concentration in the plasma versus time.
Figure 9:
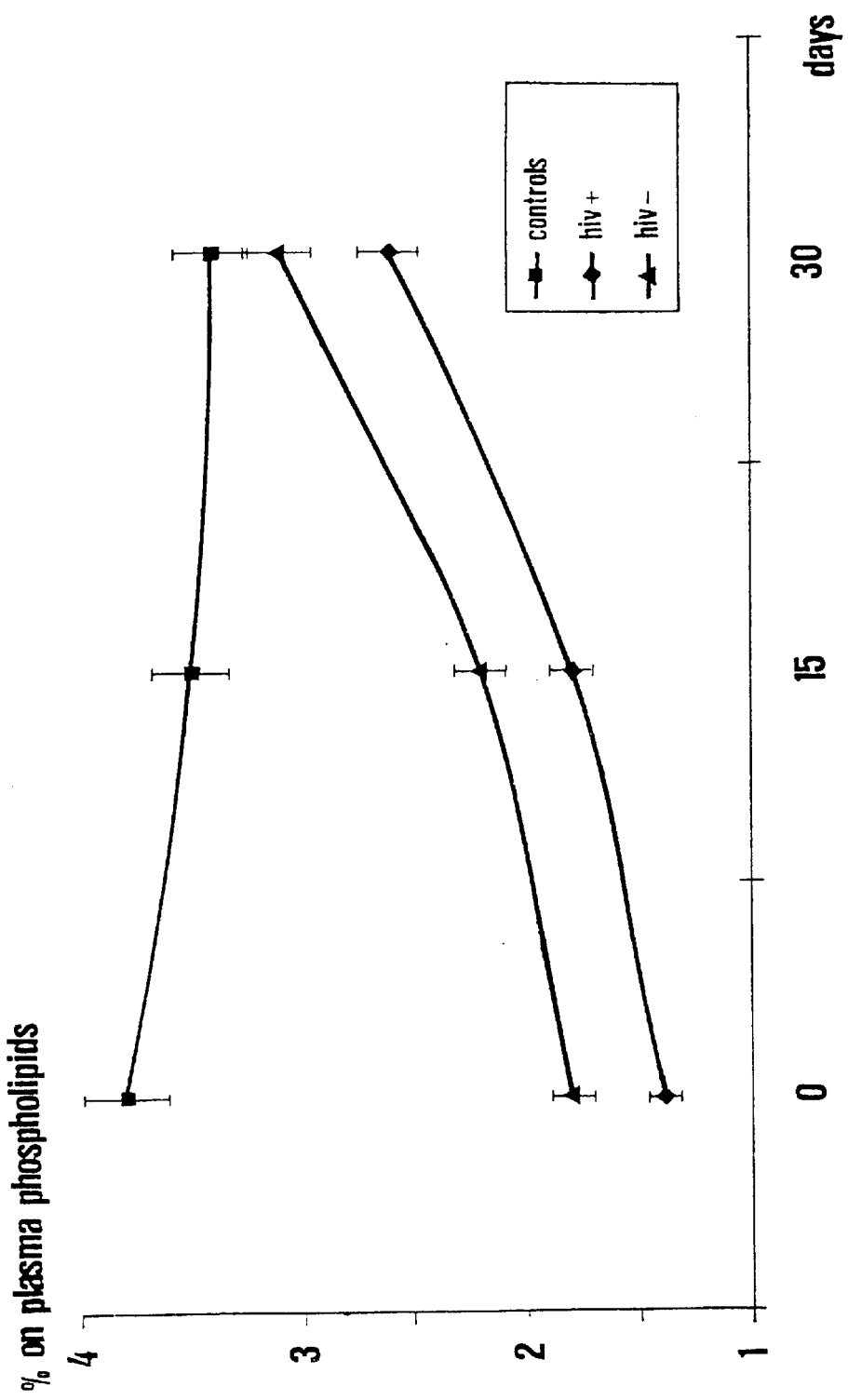
FIG. 9 shows the trend of the docosahexanoic acid concentration in the plasma versus time.

Form the results it can be observed that:

vitamin E (in the plasma and in the lymphocytes) increases both in HIV+ and in HIV− patients, and in the controls (see table 1 and FIGS. 1 and 3).

total ubiquinone (oxidized and reduced) increases significantly in HIV+ patients. Less significant increases can also be seen in HIV− patients and in the controls (see table 1 and FIG. 2).

The reduced glutathione increases significantly in HIV+ patients. Less significant increases are also found in HIV− patients and in the controls (see table 1 and FIG. 4).

The glutathione peroxidase increases in HIV+ and HIV− patients. It remains stable in the controls (see table 1 and FIG. 5).

The palmitic acid decreases significantly in HIV+ and HIV− patients. It remains stable in the controls (see table 2 and FIG. 6).

The diomo-gamma-linolenic, arachidonic and docohexaenoic acids increase significantly in HIV+ and HIV− patients. They remain stable in the controls (see table 2 and FIGS. 7, 8 and 9).

EXAMPLE 4

In the present example the effect of the administration of a variable daily quantity of pills (according to individual needs) of the following quali-quantitative composition at a certain number of patients better specified in the following.

The composition is the following:

| | | |
|---|---|---|
| Ubiquinone | mg | 12.50 |
| RRR-α-tocopheryl acetate 50% | mg | 26.65 |
| Soy lecithin | mg | 90.00 |
| Selenium aspartate | mg | 6.25 |
| L-methionine | mg | 50.00 |
| Other excipients to make | g | 1.50 |

The pills have been administered daily during the meals for one month to fifty volunteers males aged between 33 and 55 years. The volunteers were civil aviation pilots in service. The pilots have been chosen in order to evaluate the effect of the composition according to the present invention on patients whose work and lifestyle is known to provoke stress. For each individual at the beginning and after ninety days of treatment, the following parameters have been evaluated; as a control the values obtained on the control group analyzed at zero time and made up of healthy individuals have been chosen:

a) The plasma levels of phospholipids-polyunsaturated fatty acids, of vitamin E, of oxidized and reduced ubiquinone (total ubiquinone);

b) The lymphocyte levels of vitamin E;

c) The activity in the erythrocytes of glutathione peroxidase (GSH-PX);

d) The levels in the erythrocytes of reduced and oxidized glutathione (GSH and GS-SG).

Figure 10:
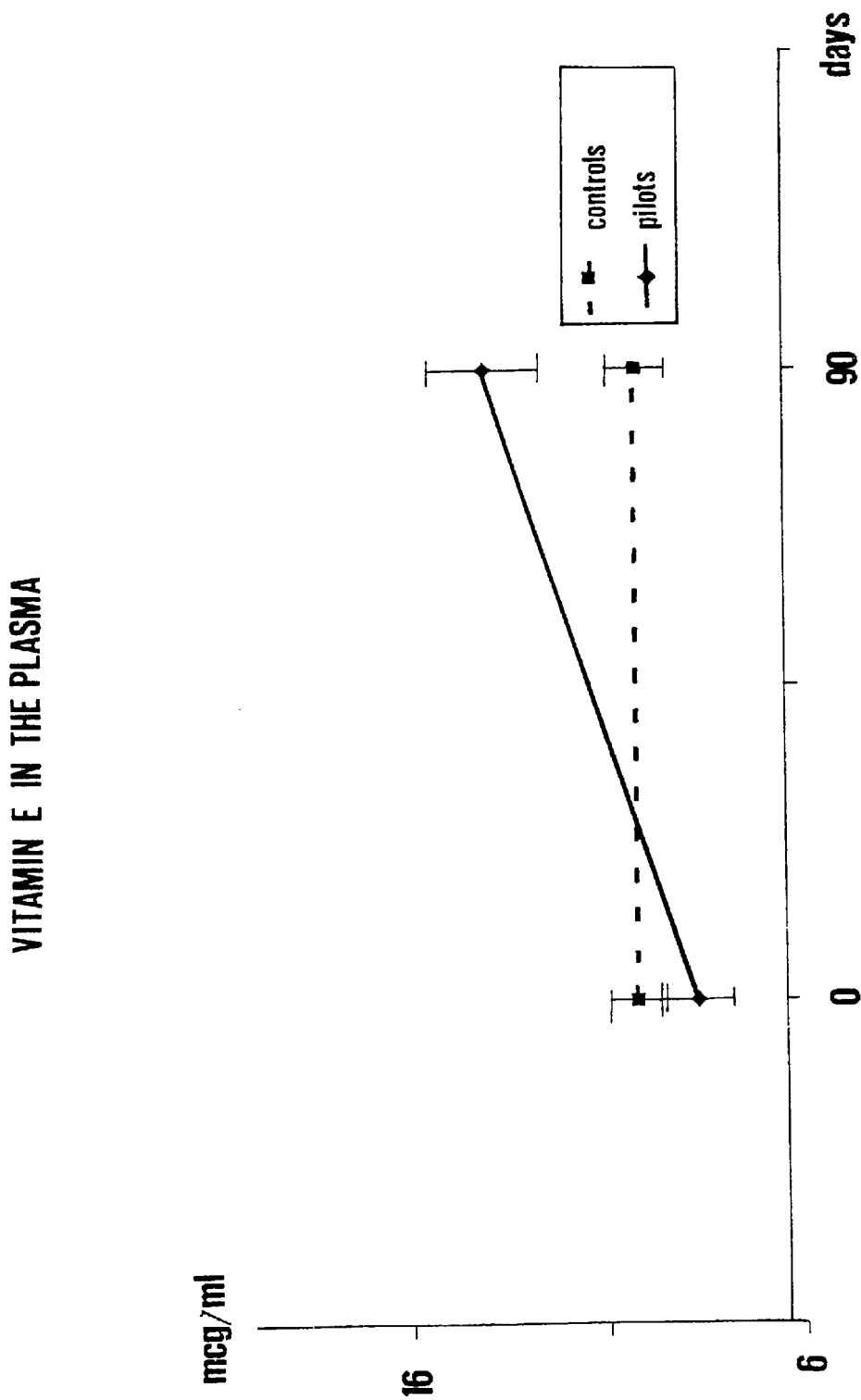
FIG. 10 shows the vitamin E concentration in the blood plasma versus time in a different population of patients form those referred to in FIG. 1 to 9.
Figure 11:
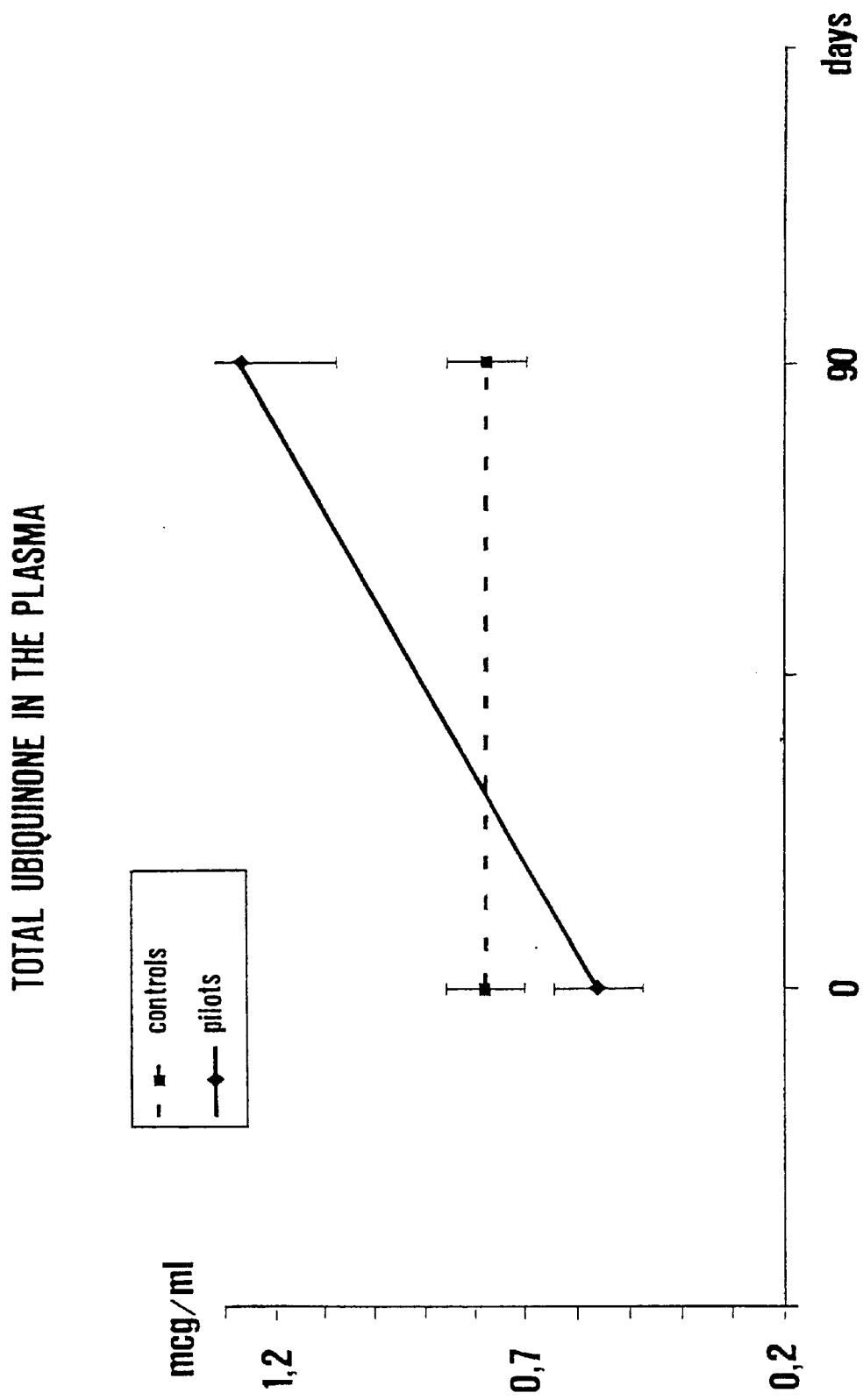
FIG. 11 shows the blood plasma concentration of total ubiquinone versus time.
Figure 12:
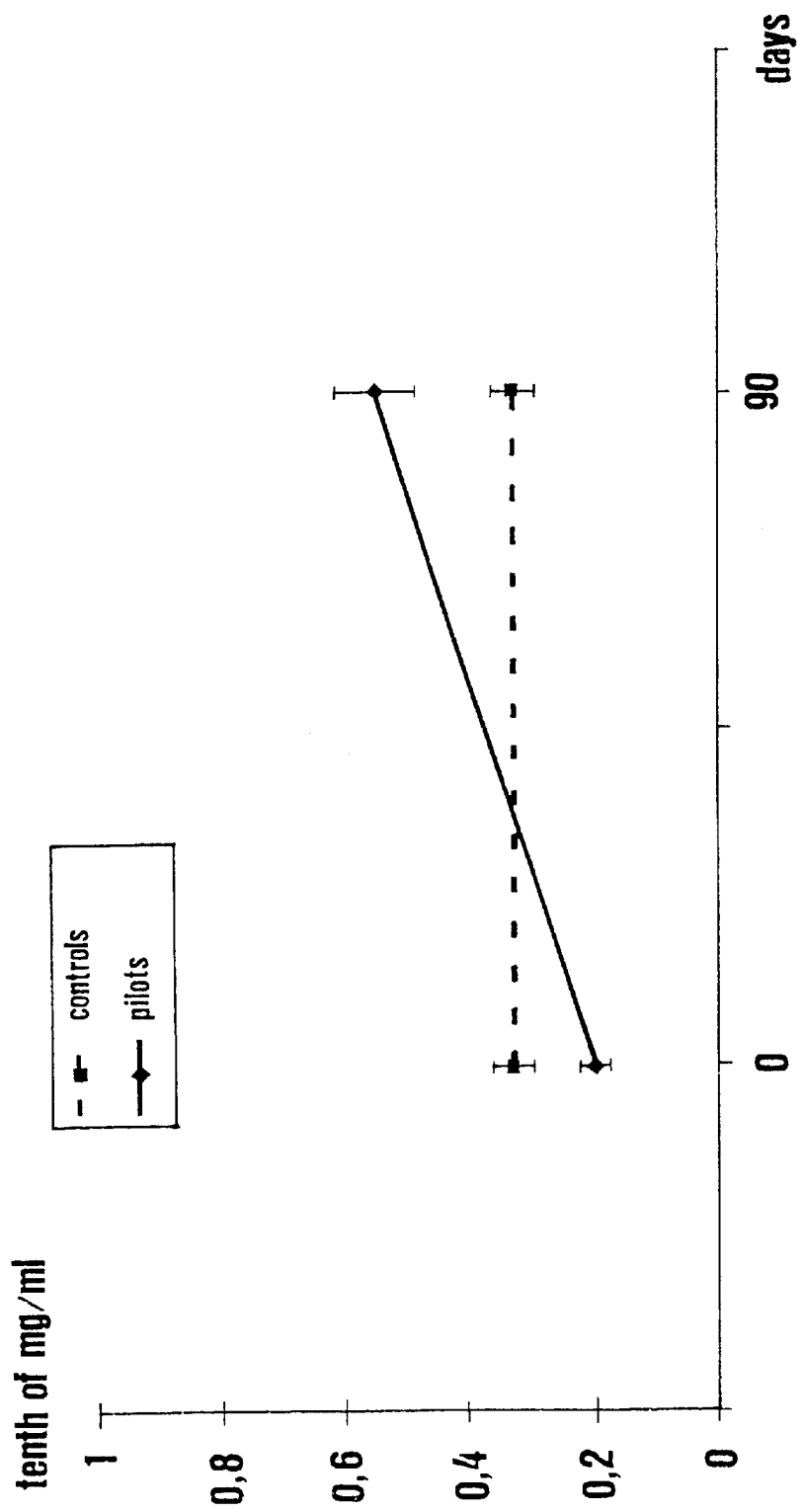
FIG. 12 shows the concentration of vitamin E in the lymphocytes versus time.
Figure 13:
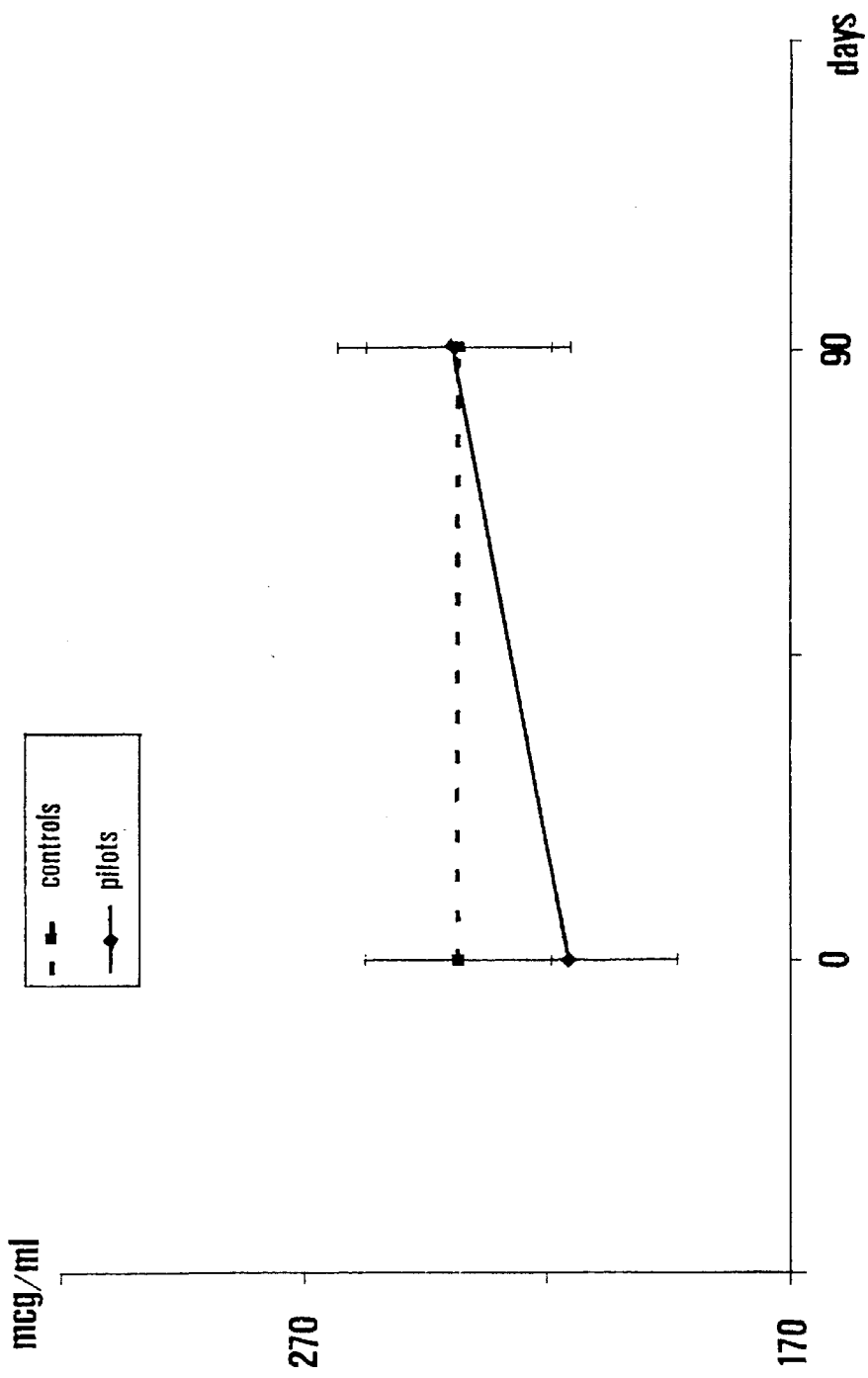
FIG. 13 shows the reduced glutathione concentration in the erythrocytes versus time.
Figure 14:
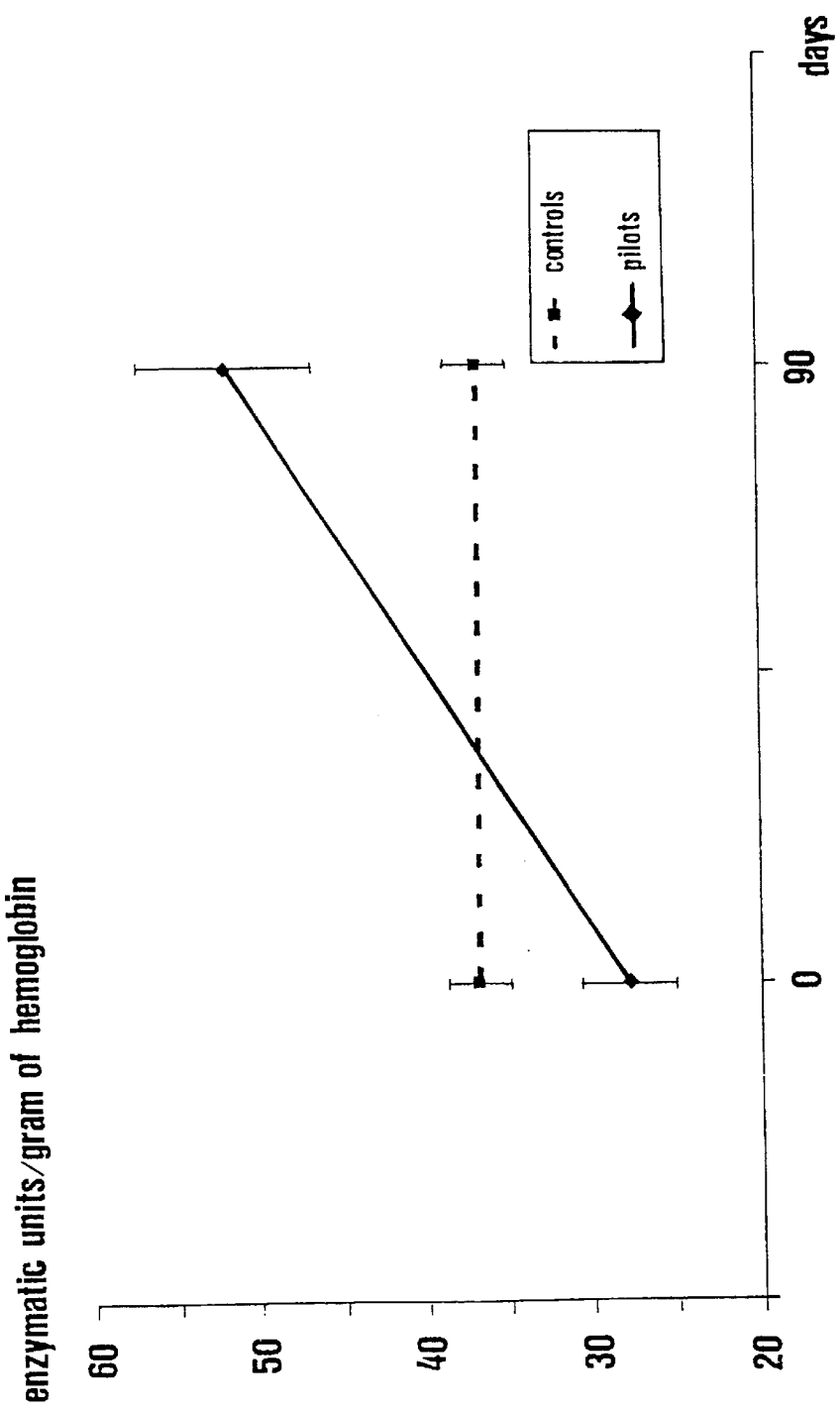
FIG. 14 shows the glutathione peroxidase concentration in the erythrocytes versus time.
Figure 15:
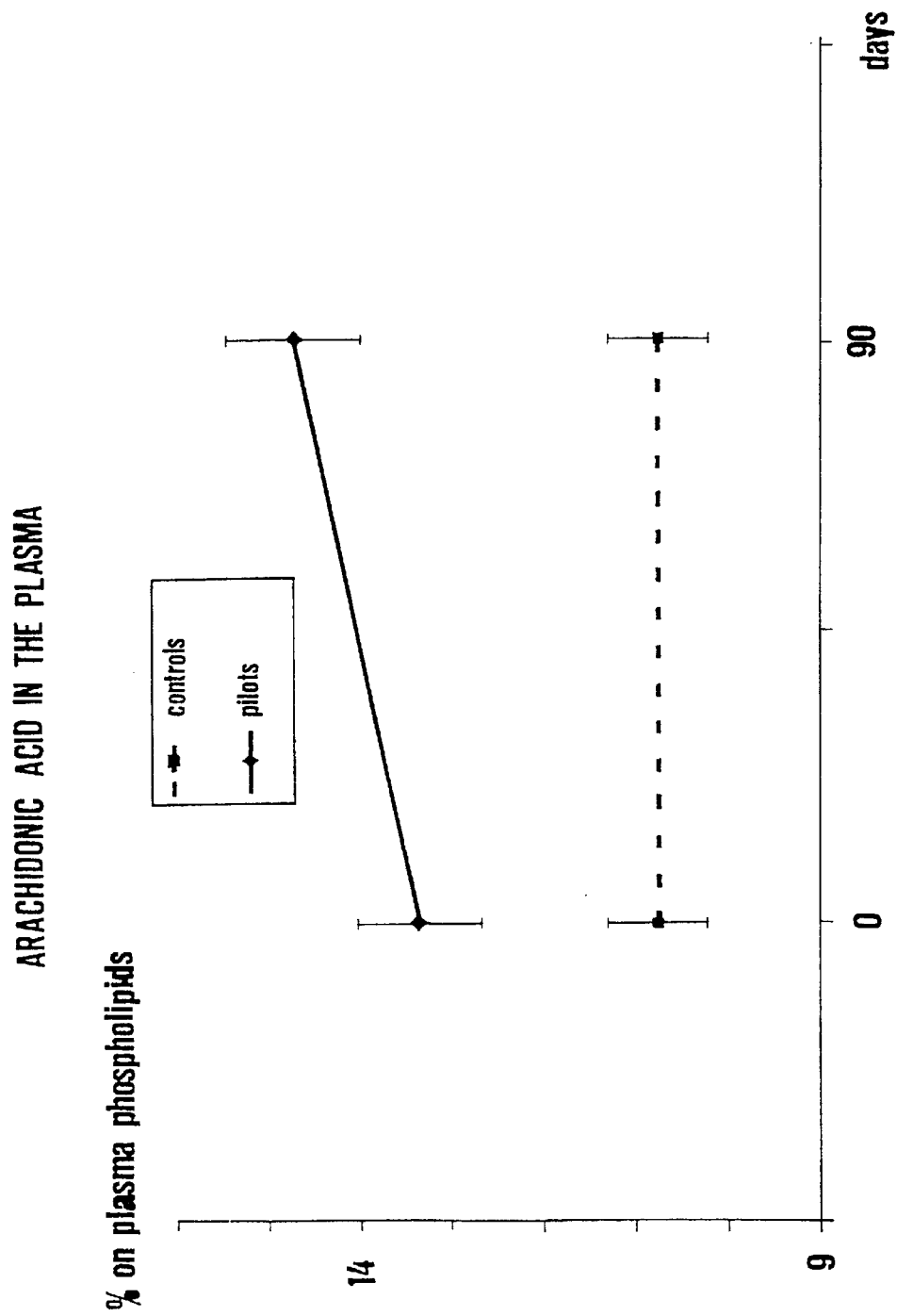
FIG. 15 shows the arachidonic acid concentration in plasma.

From the obtained results exemplified in FIGS. 10, 11, 12, 13, 14 and 15, it may be observed, at least at qualitative level, that:

vitamin E (in blood plasma and lymphocytes) increase in comparison with the control group (see FIGS. 10 and 12);

the total ubiquinone (oxidized and reduced) significantly increases in comparison with the control group (see FIG. 11);

the reduced glutathione significantly increases in comparison with the control group (see FIG. 13);

the glutathione peroxidase increases in comparison with the control group (see FIG. 14);

the arachidonic acid significantly increases in comparison with the control group (see FIG. 15).

TABLE 1

Hematic levels of antioxidants in controls and in HIV+ and HIV− patients suffering from seborrheic dermatitis before, during and after treatment with the composition according to the present invention.

| Antioxidants | CONTROLS (NO = 20) | | | HIV+ (No = 20) | | | HIV− (No = 20) | | |
|---|---|---|---|---|---|---|---|---|---|
| | t = 0 d | t = 15 d | t = 30 d | t = 0 d | t = 15 d | t = 30 d | t = 0 d | t = 15 d | t = 30 |
| PLASMA | | | | | | | | | |
| Vit. E (μg/ml) | 11.3 ± 1.9 | 15.6 ± 2.8* | 19.4 ± 4.1* | 7.9 ± 2.6* | 11.9 ± 2.7 | 15.5 ± 5.3* | 9.3 ± 1.4* | 14.7± 2.2° | 16.5 ± 3 |
| CoQ10H2 (μg/ml) | 0.48 ± 0.11 | 0.66 ± 0.09* | 0.75 ± 0.15* | 0.08 ± 0.10* | 0.15 ± 0.09* | 0.21 ± 0.11* | 0.35 ± 0.09* | 0.45 ± 0.12 | 0.56 ± 0 |
| CoQ10 (μg/ml) | 0.43 ± 0.10 | 0.47 ± 0.08 | 0.55 ± 0.08* | 0.32 ± 0.10° | 0.4 ± 0.13 | 0.74 ± 0.14* | 0.48 ± 0.11 | 0.60 ± 0.15 | 0.50 ± 0 |
| LYMPHOCYTES | | | | | | | | | |
| Vit. E (μg/ml blood) | 75 ± 21 | 88 ± 27 | 105 ± 35* | 48 ± 19+ | 53 ± 19° | 59 ± 22 | 60 ± 15° | 70 ± 23 | 86 ± 28 |
| ERYTHROCYTES | | | | | | | | | |
| GSH (μg/ml blood) | 270 ± 98 | 285 ± 90 | 297 ± 88 | 185 ± 66* | 212 ± 18° | 230 ± 70 | 240 ± 89 | 266 ± 61 | 283 ± 74 |
| GS-SG (μg/ml blood) | 23 ± 14 | 26 ± 12 | 30 ± 11 | 34 ± 15 | 30 ± 14 | 32 ± 23 | 26 ± 12 | 28 ± 10 | 27 ± 14 |
| SOD (U/g Hb) | 676 ± 141 | 66' ± 150 | 645 ± 178 | 919 ± 290* | 905 ± 180* | 891 ± 167* | 710 ± 127 | 688 ± 141 | 692 ± 14 |

TABLE 1-continued

Hematic levels of antioxidants in controls and in HIV+ and HIV− patients suffering from seborrheic dermatitis before, during and after treatment with the composition according to the present invention.

| Antioxidants | CONTROLS (NO = 20) | | | HIV+ (No = 20) | | | HIV− (No = 20) | | |
|---|---|---|---|---|---|---|---|---|---|
| | t = 0 d | t = 15 d | t = 30 d | t = 0 d | t = 15 d | t = 30 d | t = 0 d | t = 15 d | t = 30 |
| CAT (U/mg Hb) | 280 ± 33 | 275 ± 40 | 285 ± 38 | 298 ± 31 | 303 ± 42 | 314 ± 46 | 275 ± 41 | 293 ± 26 | 291 ± 33 |
| GSH-Px U/g Hb) | 708 ± 185 | 680 ± 166 | 720 ± 187 | 303 ± 200* | 346 ± 188* | 385 ± 196* | 498 ± 126* | 503 ± 163* | 608 ± 14 |

The results are expressed as an average ± SD
*$P < 0.001$ vs controls at t = 0
°$P < 0.01$ vs controls at t = 0

TABLE II

Fatty acids (%) of plasma phospholipids in controls and in HIV+ and HIV− patients suffering from seborrheic dermatitis, before, during and after treatment with the composition according to the present invention. Each result is expressed as an average ± SD

| Fatty acids | CONTROLS (No = 20) | | | HIV+ (No = 20) | | | HIV− (No = 20) | | |
|---|---|---|---|---|---|---|---|---|---|
| | t = 0 d | t = 15 d | t = 30 d | t = 0 d | t = 15 d | t = 30 d | t = 0 d | t = 15 d | t = 30 d |
| C16:0 | 26.8 ± 1.4 | 26.0 ± 2.1 | 26.2 ± 2.3 | 30.0 ± 2.1° | 29.6 ± 2.6° | 27.7 ± 2.6 | 28.5 ± 2.4 | 28.2 ± 3.0 | 26.4 ± 2.5 |
| C18:0 | 15.9 ± 1.7 | 14.2 ± 1.9 | 15.0 ± 1.8 | 18.8 ± 2.7° | 18.6 ± 4.0° | 16.4 ± 3.1 | 18.0 ± 2.6 | 17.0 ± 2.4 | 15.8 ± 2.7 |
| C18:1 | 13.1 ± 2.2 | 14.3 ± 2.0 | 13.9 ± 1.7 | 15.8 ± 2.6° | 14.8 ± 3.1 | 14.3 ± 2.5 | 15.0 ± 3.3 | 14.6 ± 2.8 | 114.3 ± 2.0 |
| C18:2 n-6 | 25.3 ± 2.3 | 24.8 ± 3.1 | 24.6 ± 3.4 | 23.9 ± 5.2 | 23.5 ± 2.5 | 24.1 ± 3.2 | 24.0 ± 6.1 | 24.0 ± 3.2 | 24.5 ± 3.0 |
| C18:3 n-6 | 3.9 ± 0.6 | 3.8 ± 1.0 | 3.7 ± 0.8 | 1.9 ± 0.1* | 2.0 ± 0.5* | 2.9 ± 0.7° | 2.3 ± 0.5* | 2.6 ± 0.7* | 3.3 ± 1.1 |
| C20:4 n-6 | 12.7 ± 1.8 | 12.4 ± 1.5 | 12.2 ± 1.8 | 7.7 ± 2.8 | 8.4 ± 2.5* | 10.9 ± 1.5° | 9.5 ± 2.4* | 10.3 ± 1.6* | 12.3 ± 1.7 |
| C22:6 n-3 | 3.8 ± 0.9 | 3.5 ± 0.7 | 3.4 ± 0.7 | 1.4 ± 0.1* | 1.8 ± 0.4* | 2.6 ± 0.5* | 1.8 ± 0.6* | 2.2 ± 0.8* | 3.1 ± 0.9 |
| others | 1.2 | 1.0 | 1.0 | 0.5 | 1.3 | 1.2 | 0.8 | 0.9 | 0.5 |

*$P < 0.001$ vs controls at t = 0
°$p < 0.01$ vs controls

Bibliography
1. HALLIWELL B., GUTTERIDGE J. M. C.: Free radicals in Biology and Medicine, $2^{nd}$. Ed. Oxford Univ. Press (Clarendon), Oxford, 1989.
2. GUTTERIDGE J. M. C., HALLIWELL B.: Antioxidant in nutrition, health and disease, Oxford Univ. Press, Oxford N.Y. Tokyo, 1994.
3. FREI B., KIM M. C., AMES B. N., Ubiquinol-10 is an effective lipid soluble antioxidant at physiological concentrations. Proc. Natl. Acad. Sci-USA 87, 4878, 1990.
4. MOHR D., BOWRY V. W., STOCKER R., Dietary supplementation with coenzyme Q10 results in increased levels of ubiquinol-10 within circulating lipoproteins and increased resistance of human low-density lipoprotein to the initiation of lipid peroxidation. Biochim. Biophys. Acta 1126, 247, 1992.
5. ERNSTER L., FORSMARK P., NORDENBRAND K.: The mode of action of lipid-soluble antioxidants in biological membranes: relationship between the effects of ubiquinol and vitamin E as inhibitors of lipid peroxidation in submitochondrial particles. BioFactors 3, 241, 1992.
6. STOCKER R., BOWRY V. W., FREI B.: Ubichinol-10 protects human low density lipoprotein more efficiently against lipid peroxidation than does α-tocopherol. Proc. Natl. Acad. Sci USA 88, 1646, 1991.
7. KAGAN V., SERBINOVA E., PACKER L.: Antioxidant effects of ubiquinones in microsomes and mitochondris mediated by tocopherol recycling. Biochem Biophys Res Commun 169, 851, 1990.
8. PASSI S., MORRONE A., PICARDO M., DE LUCA C., IPPOLITO F.: Blood levels of vitamin E polyunsatured fatty acids of phospholipids, lipoperoxides and glutathione peroxidase in patients affected with seborrheic dermatitis. J. Dermatol Sci 2, 171, 1991.
9. PASSI S., PICARDO M., DE LUCA C., MORRONE A., TERMINALI O., IPPOLITO F.: Blood levels of vitamin E polyunsaturated fatty acids of phospholipids and glutathione peroxidase activity in patients with atopic dermatitis. In: Immunological and Pharmacological aspects of atopic and contract eczema. J. M. Czernielewski ed. Pharmacology and the Skin, vol. 4, 173, 1991.
10. PASSI S., PICARDO M., MORRONE A., DE LUCA C., IPPOLITO F., ROSSI L., ROTILIO G.: Study on plasma polyunsatured phospholipids and vitamin E and on erythrocyte glutathione peroxidase in high risk HIV infection categories and AIDS patients, Clin Chem & Enzimol Comm 5, 169, 1993.
11. PASSI S.: Biochemical aspects of seborrheic dermatitis. Boll Ist Dermatologico S. Gallicano, vol. XIV, 19, 1994.
12. PASSI S., IPPOLITO F.: AIDS nuova frontiera, Lombardo editore, 1995.
13. TAKADA M., IKENOYA S., YUZURIHA R., KATAYAMA K.: Simultaneous determination of reduced and oxidised ubiquinol, Methods Enzymol. 105, 147, 1984.
14. REED D. J., BABSON J. R., BEATTY P. W., BRODIE A. E., ELLIS W. W., POTTER D. W.: High performance liquid chromatography analysis of nanomole levels of glutathione disulphide and related thiols and disulphides. Annal Biochem 106, 55, 1980.

15. L'ABBE' M. R., FISCHER P. W. F.: Automated assay of superoxide dismutase in blood. Methods Enzymol 186, 232, 1990.

16. PAGLIA D.E., VALENTINE U. N.: Studies on quantitative and qualitative characterization of erythrocyte glutathione peroxidase. J. Lab. Clin. Med. 70, 158, 1967.

17. AEBI H.: catalase in vitro. Methods Enzymol. 105, 121, 1984.

18. RISS G., KORSMANA A. W., GLINZ E., WALTHER W., RANAIDER U. B.: Separation of the eight stereoisomers of all-α-tocopherol from tissues and plasma chiral phase high performance liquid chromatography and capillary gas chromatography. Methods Enzymol 234, 302, 1994.

19. JAYARAMAN J., RAMASARMA F.: Intracellular distribution of coenzyme Q in rat liver. Arch Biochem Biophys 103, 258, 1963.

20. KALEN A., NORLING B., APPELKVIST E. L., DALLNER G.: Ubiquinone biosynthesis by the microsomal fraction from rat liver. Biochim Biophys Acta 926, 70, 1987.

21. CRANE F.L., MORRE' D. J.: Evidence for coenzyme Q function in Golgi membranes, In. Folkers K. and Yamamura Y. Biomedical and clinical aspects of coenzyme Q. vol. 1. Elsevier, Amsterdam 3–14, 1977.

22. HAMSEN A. E.: Serum lipids in eczema and other pathological conditions, Am J. Dis Child 53, 933, 1937.

23. Vitamin E.: biochemical, haematological and clinical aspects, Inc. Annals of the New York Academy of Sciences, Lubin B. and Machlin L. S. eds, vol. 393, 1982.

24. CUTLER R.G.: Antioxidants, ageing, and longevity. In: Free Radicals in Biology, Edited by Pryor A. W., Academic Press, New York-London, 371, 1984.

25. BENEDICH A.: Antioxidant vitamins and immune responses, In: Nutrition and Immunology, edited by Chandra R. K. Liss, N.Y., 125, 1988.

26. BENEDICH A., GABRIEL E., MACHIIN I. I.: Dietary vitamin E requirement for optimum immune response in rat. J. Nutr 116, 675, 1986.

27. CORWIN L. M., GORDON R. K.: Vitamin E and immune regulation. Ann NY Acad Sci 393, 437, 1982.

28. MEYDANI S. N., MEYDANI M., VERDON C. P. et al.: Vitamin E supplementation suppresses prostaglandin E synthesis and enhances the immune system of aged mice. Mech Ageing De, 34, 192, 1986.

29. INFANTE J. P.: Vitamin E and selenium participation in fatty acid desaturation. A proposal for an enzymatic function of these nutrients. Molec. Cell Biochem. 69, 93, 1986.

30. CUTLER E. G. In: Free radicals in biology (W. A. Pryor, Ed.), vol. VI, 371, Academic Press, New York, 1984.

What is claimed is:

1. A dietary composition comprising

| | |
|---|---|
| Ubiquinone | 5–8% |
| RRR-α-tocopherol acetate 50% | 12–15% |
| a Polyunsaturated phospholipid | 45–52% |
| Organic selenium (corresponding to 0.1–3% ionic selenium) | 2–5% |
| L-methionine | 23–32% | as active components along with at least one optional dietary acceptable vehicle, the percentage by weight being expressed as a percentage with reference to the total weight of the active ingredients in the composition.

2. A pharmaceutical composition for a dietary product comprising:

| | |
|---|---|
| Ubiquinone | 5–8% |
| Stabilized vitamin E | 12–15% |
| Polyunsaturated phospholipids | 45–52% |
| Organic selenium | 2–5% |
| L-methionine | 23–32% | along with pharmaceutically tolerated vehicles, the percentages by weight being expressed as a percentage by weight with reference to the total weight of the active ingredients in the composition.

3. A dietary composition according to claim 1, wherein said polyunsaturated phospholipid comprises soy lecithin, said organic selenium comprises selenium aspartate.

4. A dietary composition according to claim 1, consisting essentially of single active components in the following percentages:

| | |
|---|---|
| Ubiquinone | 6.74% |
| RRR-α-tocopheryl acetate 50% | 14.37% |
| Soy lecithin | 48.54% |
| Selenium aspartate | 3.37% |
| L-methionine | 26.97% | along with at least one dietary tolerable vehicle the percentages being expressed as percentages by weight with reference to the total weight of the active components in the composition.

5. A pharmaceutical composition according to claim 2, wherein said polyunsaturated phospholipid comprises soy lecithin, said organic selenium comprises selenium aspartate and said stabilised vitamin E comprises 50% RRR-α-tocopherol acetate.

6. A pharmaceutical composition according to claim 2, consisting essentially of single active components in the following percentages:

| | |
|---|---|
| Ubiquinone | 6.74% |
| RRR-α-tocopheryl acetate 50% | 14.37% |
| Soy lecithin | 48.54% |
| Selenium aspartate | 3.37% |
| L-methionine | 26.97% | along with at least one pharmaceutically acceptable vehicle, the percentages being expressed as percentages by weight with reference to the total weight of the active components in the composition.

7. A pharmaceutical composition as claimed in claim 2, formulated as a chewable pill.

8. A pharmaceutical composition as claimed in claim 5 formulated as a chewable pill.

9. A pharmaceutical composition according to claim 6 formulated as a chewable pill.

10. A method for combating oxidative stress and cell decay in a person in need thereof, comprising administering to said person an amount sufficient therefor of a dietary composition according to claim 1.

11. A method for combating oxidative stress and cell decay in a person in need thereof, comprising administering to said person an amount sufficient therefor of a dietary composition according to claim 3.

12. A method for treating a condition selected from the group consisting of apoptosis, mutagenesis mechanisms, carcinogenesis mechanisms, acquired immunodeficiency conditions, congenital immunodeficiency conditions, conditions of myelinic origin, and conditions deriving from a progressive alteration in the neurotransmission mechanisms, comprising administering to a patient in need of said treatment a dietary composition according to claim 1 in an amount sufficient for said treatment.

13. A method for treating a disease selected from the group consisting of diseases of myelinic origin, skin disease, and cardiovascular diseases comprising administering to a patient in need of said treatment a dietary composition according to claim 1 in an amount sufficient for said treatment.

14. A method for treating a condition selected from the group consisting of apoptosis, mutagenesis mechanisms, carcinogenesis mechanisms, acquired immunodeficiency conditions, congenital immunodeficiency conditions, conditions of myelinic origin, and conditions deriving from a progressive alteration in the neurotransmission mechanisms, comprising administering to a patient in need of said treatment a dietary composition according to claim 3 in an amount sufficient for said treatment.

15. A method for treating a disease selected from the group consisting of diseases of myelinic origin, skin disease, and cardiovascular diseases comprising administering to a patient in need of said treatment a dietary composition according to claim 3 in an amount sufficient for said treatment.

16. A method for treating a disease selected from the group consisting of infectious diseases of viral or bacterial origin and diseases deriving from external pathogens other than viruses or bacteria, comprising administering to a patient in need of said treatment a dietary composition according to claim 1 in an amount sufficient for said treatment.

17. The method according to claim 16 wherein the diseases is selected from the group consisting of tuberculosis, leprosy, herpes simplex labialis, herpes simplex genetalis, AIDS, multiple sclerosis, atopic dermatitis, and vitiligo.

18. A method for vaccinating a mammal against allergies comprising administering to a mammal in need thereof an effective amount of a dietary composition according to claim 1.

19. A method for treating a disease selected from the group consisting of infectious diseases of viral or bacterial origin and diseases deriving from external pathogens other than viruses or bacteria, comprising administering to a patient in need of said treatment a dietary composition according to claim 1 in an amount sufficient for said treatment.

20. The method according to claim 16 wherein the diseases is selected from the group consisting of tuberculosis, leprosy, herpes simplex labialis, herpes simplex genetalis, AIDS, multiple sclerosis, atopic dermatitis, and vitiligo.

21. A method for vaccinating a mammal against allergies comprising administering to a mammal in need thereof an effective amount of a dietary composition according to claim 3.

* * * * *